(12) United States Patent
Tapanes

(10) Patent No.: US 8,873,064 B2
(45) Date of Patent: Oct. 28, 2014

(54) FIBER-OPTIC DISTURBANCE DETECTION USING COMBINED MICHELSON AND MACH-ZEHNDER INTERFEROMETERS

(75) Inventor: Edward Tapanes, Hillsboro, OR (US)

(73) Assignee: Fibersonics Inc., Hillsboro, OR (US)

( * ) Notice: Subject to any disclaimer, the term of this patent is extended or adjusted under 35 U.S.C. 154(b) by 372 days.

(21) Appl. No.: 13/499,274

(22) PCT Filed: Sep. 21, 2011

(86) PCT No.: PCT/US2011/052608
§ 371 (c)(1),
(2), (4) Date: Mar. 29, 2012

(87) PCT Pub. No.: WO2012/050774
PCT Pub. Date: Apr. 19, 2012

(65) Prior Publication Data
US 2012/0224182 A1  Sep. 6, 2012

Related U.S. Application Data

(60) Provisional application No. 61/393,298, filed on Oct. 14, 2010, provisional application No. 61/393,321, filed on Oct. 14, 2010.

(51) Int. Cl.
*G01B 9/02* (2006.01)
*G02B 6/36* (2006.01)
*G02B 6/255* (2006.01)

(52) U.S. Cl.
CPC .............. *G01B 9/02* (2013.01); *G01B 9/02012* (2013.01); *G01B 2290/70* (2013.01); *G01B 9/02027* (2013.01); *G02B 6/36* (2013.01); *G01B 9/02079* (2013.01); *G02B 6/255* (2013.01)

USPC .............................................. 356/478; 385/13

(58) Field of Classification Search
CPC ........... G01B 9/02012; G01B 9/02079; G01B 9/02027; G01B 9/02; G01B 2290/70; G02B 6/36; G02B 6/255
USPC ................................ 356/450–521; 385/12, 13
See application file for complete search history.

(56) References Cited

U.S. PATENT DOCUMENTS

| 4,725,141 | A |   | 2/1988 | Georgiou et al. |
| 4,770,535 | A | * | 9/1988 | Kim et al. ..................... 356/478 |
| 5,473,459 | A |   | 12/1995 | Davis |
| 5,798,834 | A | * | 8/1998 | Brooker ........................ 356/477 |
| 6,289,740 | B1 | * | 9/2001 | Posey et al. ..................... 73/800 |

(Continued)

*Primary Examiner* — Tarifur Chowdhury
*Assistant Examiner* — Michael P Lapage
(74) *Attorney, Agent, or Firm* — Schwabe Williamson & Wyatt

(57) ABSTRACT

A fiber-optic sensor can have a Michelson sensor portion and a Mach-Zehnder sensor portion. A first splitter-coupler can be configured to split incoming light between a first fiber portion and a second fiber portion. A first polarization-phase conjugation device can be configured to conjugate a polarization phase of incident light corresponding to the first fiber portion, and a second polarization-phase conjugation device can be configured to conjugate a polarization phase of incident light corresponding to the second fiber portion. Each of the first and second polarization-phase conjugation devices can be configured to reflect light toward a detector and through the respective first and second fiber portions. A coupler can be configured to join light in the first fiber portion with light in the second fiber portion, and a third fiber portion can be configured to receive light from the coupler and to illuminate a second detector.

18 Claims, 8 Drawing Sheets

(56) References Cited

U.S. PATENT DOCUMENTS

| | | |
|---|---|---|
| 6,842,254 B2 | 1/2005 | Van Neste et al. |
| 7,106,450 B2 * | 9/2006 | Jensen et al. .................. 356/477 |
| 2002/0118368 A1 | 8/2002 | Tsuda |
| 2003/0053069 A1 * | 3/2003 | Motamedi et al. ............ 356/477 |
| 2006/0038115 A1 * | 2/2006 | Maas ....................... 250/227.18 |
| 2006/0182383 A1 | 8/2006 | Slotwinski |
| 2007/0103692 A1 * | 5/2007 | Hall et al. ..................... 356/478 |
| 2008/0193090 A1 | 8/2008 | Riddett et al. |
| 2010/0014095 A1 | 1/2010 | Patel et al. |
| 2010/0043953 A1 | 2/2010 | Riddett et al. |

* cited by examiner

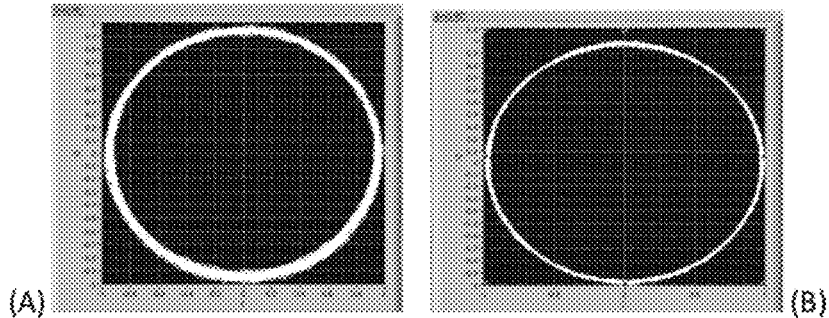

FIG. 11

| launch light into a fiber | 1201 |
| --- | --- |
| split the light into a first outbound portion and a second outbound portion | 1202 |
| split the first outbound portion into a first reflection portion and a corresponding first coupling portion | 1203 |
| split the second outbound portion into a second reflection portion and a corresponding second coupling portion | 1204 |
| reflect the first reflection portion with a first polarization-phase conjugation device and reflect the second reflection portion with a second polarization-phase conjugation device | 1205 |
| combine the first reflection portion and the second reflection portion | 1206 |
| combine the first coupling portion and the second coupling portion | 1207 |

FIG. 12

| | |
|---|---|
| launch light into a fiber-optic sensor comprising a Michelson sensor portion, a Mach-Zehnder sensor portion, and an operative coupling therebetween | 1301 |
| detect a combined first signal portion and a second signal portion from the Michelson sensor portion | 1302 |
| detect the first signal portion from the Mach-Zehnder sensor portion | 1303 |
| sense a disturbance location based on a comparison of the first signal portion and the second signal portion | 1304 |

FIG. 13

FIBER-OPTIC DISTURBANCE DETECTION USING COMBINED MICHELSON AND MACH-ZEHNDER INTERFEROMETERS

This application is a U.S. National Phase application under 35 U.S.C. §371 of International Application Serial Number PCT/US11/052608 filed Sep. 21, 2011, which also claims the benefit of U.S. Provisional Patent Application Ser. No. 61/393,298 and U.S. Provisional Patent Application Ser. No. 61/393,321, both filed Oct. 14, 2010, the contents of which are hereby incorporated by reference as if recited in full herein for all purposes.

BACKGROUND

The innovations disclosed herein pertain to interferometer systems, and more particularly, but not exclusively, to fiber-optic interferometer systems, such as, for example, systems used in security, surveillance or monitoring applications. Some disclosed interferometer systems relate to detecting and locating disturbances (e.g., a disturbance to a secure perimeter, such as a "cut" on a fence, a leak from a pipeline, a change in structural integrity of a building, a disturbance to a communication line, a change in operation of a conveyor belt, an impact on a surface or acoustical noise, among others) with one or more passive sensors.

Earlier attempts at using interferometer-based systems to detect disturbances have met with varying degrees of success. For example, a Mach-Zehnder interferometer can detect a phase-shift between two beams of light split from a single collimated beam. When two respective optical path lengths differ, the respective beams typically will be out of phase and a Mach-Zehnder interferometer can detect such a phase difference. Thus, a Mach-Zehnder interferometer can detect a change in relative optical-path lengths, such as can occur when one of a pair of optical conduits carrying optical signals is perturbed differently than the other of the pair. Nonetheless, a Mach-Zehnder interferometer alone cannot provide the location of such a disturbance or the magnitude of the difference in path lengths.

Systems including interferometers configured to detect a disturbance have been proposed. For example, U.S. Pat. No. 6,778,717 discloses a method that includes launching light in opposite directions through a single Mach-Zehnder interferometer to form counter-propagating optical signals that can be modified by a perturbation of the interferometer (also referred to as a "disturbance" or an "event"). The '717 patent discloses that the position of such an event can be determined by substantially continuously and simultaneously monitoring respective modified counter-propagating optical signals and determining the time difference between the separately detected modified signals. The disclosure in the '717 patent is incorporated herein in its entirety by reference.

U.S. Pat. Nos. 7,499,176 and 7,499,177 disclose improvements to the technology disclosed in U.S. Pat. No. 6,778,717. The '176 and '177 patents are directed to methods and apparatus for actively controlling polarization states of counter-propagating optical signals passing through a Mach-Zehnder interferometer so as to match phase and/or amplitude between the counter-propagating signals. With the technology disclosed in U.S. Pat. No. 6,778,717, substantially matched polarization states are required to correlate the output corresponding to each of the counter-propagating signals to the other respective signal outputs. Such an interferometer is shown schematically in FIG. 1. The disclosure in the '176 and '177 patents are incorporated herein in their entirety by reference.

To actively control the polarization states of the counter-propagating signals, a polarization controller is needed at each input of the Mach-Zehnder interferometer's light paths. Such polarization controllers that provide matched polarization states are costly. Also, since at least some polarization controllers are configured to tune polarization states so that observed output signals have no amplitude- or phase-shift between them, when a sensor is momentarily perturbed and a polarization-induced phase-shift between counter-propagating signals is thereby introduced, a significant amount of time can elapse after the perturbation and before the polarization controllers have suitably matched polarization states to detect a subsequent perturbation. Therefore, a significant amount of time can elapse before a subsequent disturbance can be detected and located accurately.

Therefore, systems as disclosed in U.S. Pat. Nos. 7,499,176, 7,499,177 and 6,778,717 suffer serious deficiencies. For example, perimeter security systems incorporating such systems can be bypassed by introducing a diversionary disturbance at one location and subsequently crossing a monitored perimeter at another location some distance away from the location of the diversionary disturbance while the polarization controllers are being "reset" (e.g., are attempting to re-match polarization states).

Other approaches for detecting disturbances have also been proposed. For example, U.S. Pat. No. 7,514,670, describes a low-cost system having a distributed plurality of sensitive "zones." In particular, the '670 patent discloses a system having an optical conduit configured to convey light past a plurality of sensitive regions and to split off a fraction of light into each of the sensitive regions. Each of the sensitive regions comprises, for example, an interferometer configured to detect a disturbance.

Since a portion of an incoming beam of light is diverted into each sensitive region (or zone), such a system has practical limitations on the number of zones that are possible when using a given light source. As a result of being limited to a particular number of zones, there is also a practical limitation on the length of a perimeter that can be monitored with such a system.

The '670 patent discloses that the presence of a disturbance can be isolated to a particular zone, so such a system can generally identify the location of a disturbance. However, such a zone can span a relatively large distance, which might not provide a desired spatial resolution for many security applications. For example, some security applications require that a system identify the location of a disturbance to within several (e.g., less than about ten) meters (such as, for example, to within between about 3 meters and about 5 meters).

Thus, a need remains for simpler and less costly systems for accurately detecting the existence, position or magnitude of a disturbance. There also remains the need for systems that provide these advantages over a distance of many kilometers. There also remains the need for systems that can detect the existence, position or magnitude of a subsequent disturbance within fewer than about 3 seconds of an initial event or disturbance.

SUMMARY

Innovative interferometer systems that overcome one or more of the foregoing or other needs are described. Some embodiments of such innovative systems comprise an apparatus configured to detect a disturbance (sometimes referred to as an "event" or a "target") to an optical conduit. In some instances, the presence of a disturbance, together with a position of the disturbance, can be detected. Some innovative systems comprise a method for detecting such a disturbance and its position. With some embodiments of such innovative systems, a magnitude of such a disturbance can also be determined. For example, some disclosed embodiments of optical (e.g., fiber optic) sensor systems provide one or more of the following advantages over distances up to and even more than about 50 km away from active circuitry using passively terminated fiber optic sensors:

(1) detecting the presence of a disturbance;
(2) detecting a position of the disturbance; and
(3) detecting a magnitude of the disturbance.

Some innovative systems can provide these and other advantages over distances up to, for example, about 65 kilometers (km) with one passive sensor, and up to, for example, about 130 km with first and second passive sensors extending in opposite directions.

These and other previously unattainable advantages are made possible, at least in part, by an innovative interferometer-based sensor incorporating aspects of a Michelson sensor with aspects of a Mach-Zehnder sensor.

In some innovative systems, the Michelson sensor portion includes a first fiber portion and a second fiber portion. A first splitter-coupler can be configured to split incoming light between the first fiber portion and the second fiber portion. A first polarization-phase conjugation device can be configured to conjugate a polarization phase of incident light corresponding to the first fiber portion, and a second polarization-phase conjugation device can be configured to conjugate a polarization phase of incident light corresponding to the second fiber portion. Each of the first and second polarization-phase conjugation devices can be configured to reflect light toward a detector (sometimes referred to as a "Michelson detector") and through the respective first and second fiber portions. The Michelson detector can be positioned adjacent respective proximal ends of the first and the second conduits, and the respective polarization-phase conjugation devices can be positioned adjacent the respective distal ends of the first and the second conduits.

In some innovative systems, the Mach-Zehnder sensor portion includes the first fiber portion and the second fiber portion, and the first splitter-coupler configured to split incoming light between the first fiber portion and the second fiber portion. A coupler can be configured to join a portion of light in the first fiber portion with a portion of light in the second fiber portion, and a third fiber portion can be configured to receive light from the coupler and to illuminate a second detector (sometimes referred to as a "Mach-Zehnder detector"). Light that passes through the third fiber portion can illuminate the second detector independently of light reflected by the first or second polarization-phase conjugation devices.

In some instances, innovative interferometer systems also include a polarization scrambler configured to alter a polarization state of light entering the first and second fiber sensor portions. The scrambler can intermittently (e.g., selectively, periodically or aperiodically) alter the polarization so as to maintain a suitable signal-to-noise ratio at the Mach-Zehnder detector (e.g., through the Mach-Zehnder sensor portion of the innovative interferometer).

The first fiber portion and the second fiber portion can extend longitudinally of one passively terminated fiber optic cable. A proximal end of the fiber optic cable can be configured to couple to the first detector such that the Michelson sensor portion can illuminate the first detector. The proximal end of the fiber optic cable can be configured to couple to the second detector such that the Mach-Zehnder sensor portion can illuminate the second detector. The operative coupling between the Michelson sensor portion and the Mach-Zehnder sensor portion can be positioned adjacent a distal end of the fiber optic cable. The respective polarization-phase conjugation devices can be positioned adjacent a distal end of the fiber optic cable. Such a passively terminated fiber optic cable can extend up to about 65 km away from the first and second detectors, such as, for example, between about 40 km and about 65 km away from the detectors. In other instances, a passively terminated fiber optic cable can extend between about 1 km and about 10 km away from the first and second detectors, for example. Other distances, such as, for example, between about 10 km and about 20 km, between about 20 km and about 30 km, and between about 30 km and about 40 km are also possible.

Innovative methods of identifying the location of a disturbance are disclosed. For example, light can be launched into an interferometer-based sensor having a Michelson sensor portion, a Mach-Zehnder sensor portion, and an operative coupling therebetween. A combined first signal portion and second signal portion can be observed by the Michelson sensor portion. The first signal portion can be observed by the Mach-Zehnder sensor portion. A position of the disturbance can be determined from a comparison of the first signal portion to the second signal portion. For example, the first signal portion observed by the Mach-Zehnder sensor portion can be subtracted from the combined first signal portion and second signal portion observed by the Michelson sensor portion.

A magnitude of the disturbance can be determined, at least in part, from observed first and second signal portions, observed phase-shifts between the first signal portion and the second signal portion, or both. For example, a magnitude of the disturbance can be determined, in part, by unambiguously counting fringes, unambiguously integrating the observed phase-shift over a specified duration, or both (e.g., by averaging the respective magnitudes determined from unambiguously counting fringes and unambiguously integrating the phase changes).

Computer-readable media and computer-implementable methods are also disclosed. Such media can store, define or otherwise include computer-executable instructions for causing a computing environment to perform innovative methods as disclosed herein. Related computing environments are also disclosed and can be special purpose or general purpose computing environments.

The foregoing and other features and advantages will become more apparent from the following detailed description, which proceeds with reference to the accompanying drawings.

BRIEF DESCRIPTION OF THE DRAWINGS

The accompanying drawings show aspects of the innovating systems disclosed herein, unless specifically identified as showing a known feature from the prior art.

FIG. 11A shows a first phasor output plotted in polar coordinates. FIG. 11B shows a second phasor output plotted in polar coordinates.

FIG. 12 is a table summarizing an innovative method as disclosed herein.

FIG. 13 is a table summarizing another innovative method as disclosed herein.

DETAILED DESCRIPTION

Various principles related to interferometer systems are described herein by way of reference to exemplary systems. One or more of the disclosed principles can be incorporated in various system configurations to achieve one or more interferometer system characteristics. Systems relating to perimeter security applications are merely examples of innovative interferometer systems and are described herein to illustrate aspects of the various principles disclosed herein. Some embodiments of disclosed innovations may be equally applicable to use in many other applications, such as, for example, detecting a leak in a pipeline, detecting a failure in a structure, detecting a disturbance to a ground surface, detecting a change in operation of a conveyor, etc.

Overview of Innovative Interferometer Systems

Interferometer systems as disclosed herein can detect a disturbance to a sensor portion by comparing a phase shift between observed first and second optical signals that have travelled through a first (e.g., a "reference") optical conduit and a second (e.g., a "sensor") optical conduit.

Figure 1:
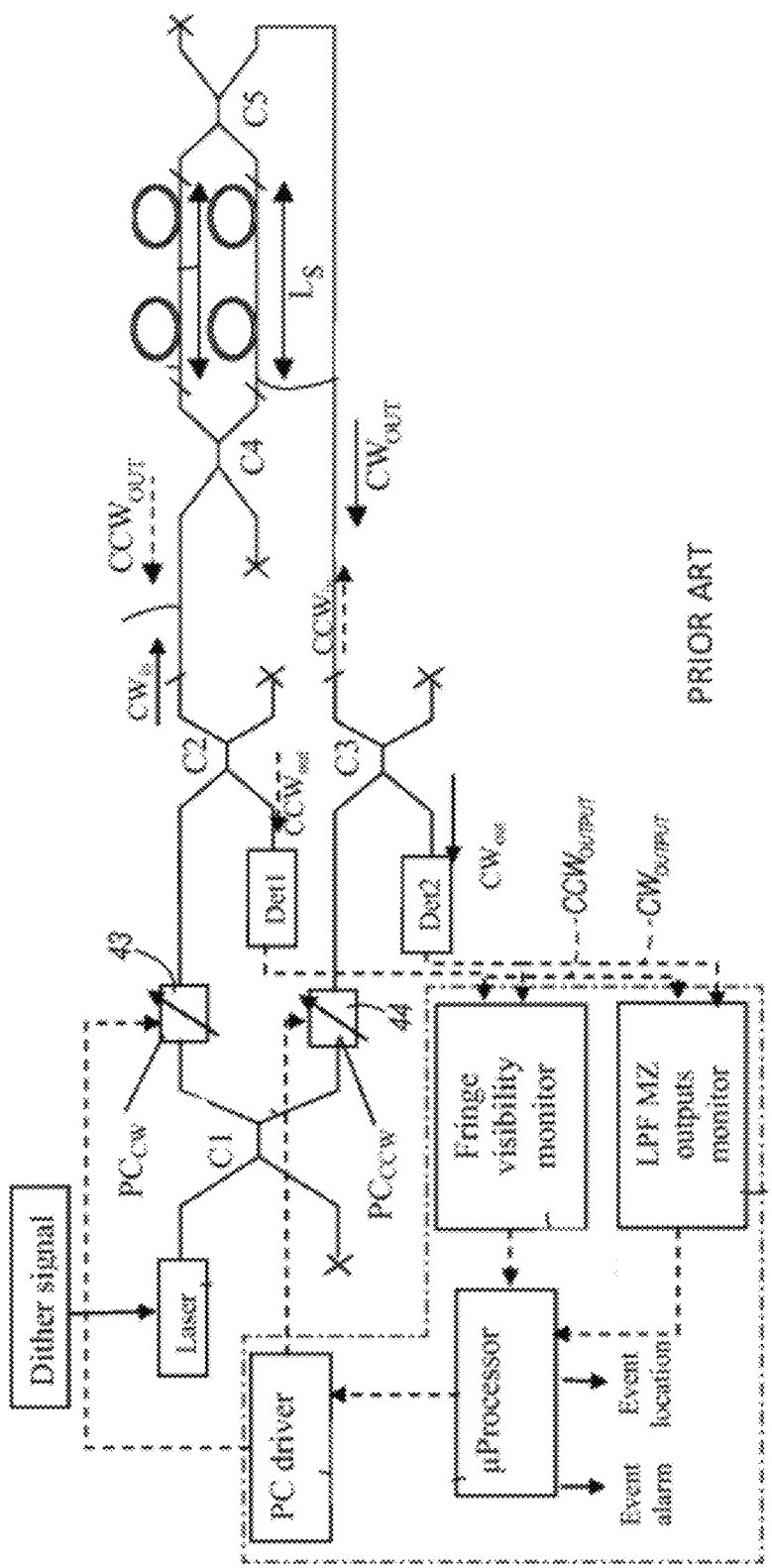
FIG. 1 shows a schematic illustration of a commercially available Mach Zehnder interferometer configured to use counter-propagating optical signals having actively matched polarization states.
Figure 2:
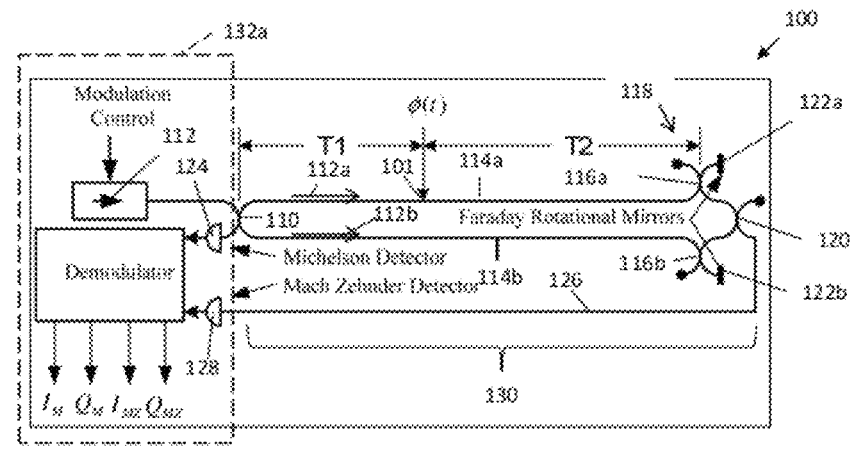
FIG. 2 shows aspects of an innovative interferometer of the type disclosed herein.

For example, the innovative interferometer 100 shown in FIG. 2 has a first splitter/coupler 110 configured to split modulated light (indicated by arrows 112a, 112b) into first and second optical conduits 114a, 114b (e.g., fiber-optic fibers, such as, for example, single-mode fiber optic fibers). First and second terminal splitters/couplers 116a, 116b positioned adjacent a distal (terminal) end 118 of the respective first and second conduits are configured to direct a portion of light in the conduits to either (1) another coupler 120 (referred to herein as a "Mach-Zehnder coupler") configured to recombine light from the first and second conduits 114a, 114b, or (2) respective first and second polarization-phase conjugation devices 122a, 122b that are configured to conjugate a polarization phase of incident light. An example of such a polarization-phase conjugation device 122a, 122b is a Faraday rotational mirror, as indicated in FIG. 2. A suitable Faraday rotational mirror can be obtained from OFR MF1-1310-A.

A Michelson interferometer can detect a difference in length between a first optical path and a second optical path, and thus a disturbance to one of a pair of optical paths. A Michelson interferometer splits a collimated beam of light into a pair of light beams that follow respective light paths (e.g., through an optical conduit, such as a single-mode optical fiber). At a terminal end of the respective optical paths, each respective beam is reflected such that it passes through the same respective light path a second time, albeit in an opposite direction compared to the first time the beam passed through it. A phase shift between the reflected pair of beams indicates that the respective optical paths have different optical lengths. Thus, a Michelson interferometer can be used to detect a disturbance to a pair of light paths that causes a net change in relative optical path lengths. Like a Mach-Zehnder interferometer, a Michelson interferometer alone cannot identify the location or magnitude of such a disturbance.

When arranged as shown in FIG. 2, the first splitter/coupler 110, the pair of optical conduits 114a, 114b (e.g., fibers) and respective first and second polarization-phase conjugation devices 122a, 122b form, at least in part, a Michelson interferometer portion. The respective first and second polarization-phase conjugation devices 122a, 122b, e.g., Faraday rotational minors in the embodiment shown in FIG. 2 can be configured to swap the fast and slow polarization axes of reflected light. Accordingly, a polarization state of each respective reflected beam of light returning from the respective devices 122a, 122b to the first splitter/coupler 110 through each of the conduits 114a, 114b can be conjugate to the polarization state of the light as it traveled from the splitter 110 to the devices 122a, 122b. The first splitter/coupler 110 can be configured to combine the respective beams of reflected light travelling in the respective conduits 114a, 114b and to divert a portion of the combined light to illuminate a first detector 124 (referred to herein as a "Michelson detector"). In some embodiments, the first detector is configured as a singlemode fiber pigtailed InGaAs photodiode.

Respective portions of light in the first and second conduits 114a, 114b that are directed to the Mach-Zehnder coupler 120 can be recombined by the coupler and directed into a return conduit 126 (e.g., a third single-mode fiber) optically coupled to a second detector 128 (referred to herein as the "Mach-Zehnder detector") such that an optical signal in the return conduit can illuminate the second detector. In some embodiments, the coupler 120 is a singlemode 3 dB fused coupler. As with the Michelson detector 124, the Mach-Zehnder detector can be configured as a singlemode fiber pigtailed InGaAs photodiode.

Figure 3:
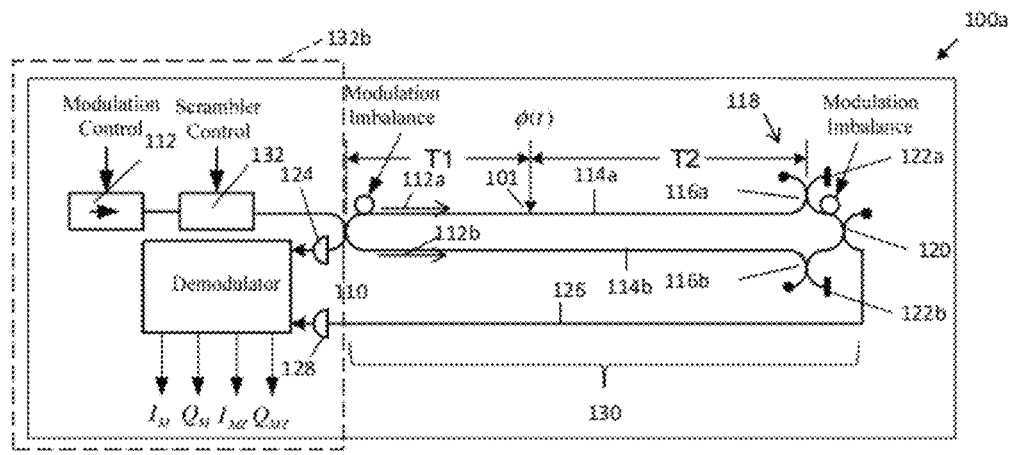
FIG. 3 shows aspects of an innovative interferometer system of the type disclosed herein.

The Mach-Zehnder detector 128 can be positioned adjacent a modulated light source (identified in FIG. 2 as "modulation control"), the Michelson detector 124, or both. Such a configuration can provide a completely passive optical sensor portion 130 extending away from an active portion 132a by as much as 50 km, or farther. As shown in FIGS. 2 and 3, the active portions 132a, 132b comprise, respectively, a modulated light source, detectors 124, 128, and a demodulator. The active portion 132b also includes a polarization scrambler. Such a light source can be a narrow line-width, singlemode pigtailed fiber laser or other laser device having a narrow line-width. A suitable modulator is an Agiltron NOPS-115111331 device. The passive portions 130 comprise optical conduits 114a, 114b, 126, polarization-phase conjugation devices 122a, 122b and the splitters/couplers 116a, 116b, 120 positioned adjacent the distal end 118.

With such an interferometer 100, a signal detected at the Michelson detector 124 can include a signal portion corresponding to the outbound light mixed and confounded with a signal portion corresponding to the inbound light reflected by the polarization-phase conjugation devices 122a, 122b. A signal detected at the Mach-Zehnder detector 128 includes a signal portion corresponding to the outbound light. (In some instances, one or more signal portions observed by the Michelson or Mach-Zehnder detectors correspond to higher-order harmonics arising from reflections. Such harmonics can be suitably filtered with low-pass filters.)

Signals from the respective detectors 124, 128 can be provided to a demodulator, and the demodulator can provide respective phasor outputs I and Q (described below) to, for example, a post-processing apparatus, such as a computing environment described below. When the phasor outputs exceed a given threshold (e.g., detect a disturbance), the post-processing apparatus can, for example, provide an alarm indicating the presence of a disturbance.

For example, if one of the optical conduits 114a, 114b is disturbed at a point 101, outbound light from the splitter/coupler 110 can reach the point 101 after a first time, T1, and a reflected portion of the light can reach the point 101 again at a second time, (T1+T2+T2). In such an instance, the optical signal sensed at the Michelson detector 124 can include a first signal portion arising from a perturbation of the outbound light mixed and confounded with a second signal portion arising from a perturbation of the inbound (reflected) light. Since the mixed and confounded first and second portions (the "Michelson signal components") are observed with a single detector 124, they cannot be observed independently. Stated differently, the two Michelson signal components (outbound and inbound) cannot be separated out from the confounded mixture.

In contrast, a signal observed at the Mach-Zehnder detector 128 can contain a signal portion arising from a perturbation of the outbound light only. Thus, in some disclosed approaches, the signal from the Mach-Zehnder detector can be subtracted from the signal observed at the Michelson detector (a confounded mixture of the first, outbound, signal portion and the second, inbound signal portion) to obtain the second signal portion. Such a second signal portion can thus be used to extract the Michelson first signal portion and this can be compared to the first signal portion observed by the Mach-Zehnder detector. A phase or time-shift between the first signal portions of each interferometer can provide a measure of the location of the disturbance, as described more fully below. Alternatively, or additionally, a comparison of the first signal portion and the second signal portion, once separated from the Michelson detector's signal, can provide a measure of the location of a disturbance. Likewise, being able to compare the first and second separated-out signal portions of the Michelson sensor can be utilized to provide a measure of the location of the disturbance.

From the phase-shift, the delay T1 between the time light is launched into the sensor 130 and the time the light reaches a point of disturbance 101 and the delay, (T1+T2+T2), between the time the light is launched into the sensor 130 and the time the light reflected by the polarization-phase conjugation devices 122a, 122b reaches the point of disturbance 101 can be determined. With knowledge of the respective delays, the position of the point of disturbance 101 along the sensor 130 can be calculated using disclosed methods. In addition, a magnitude of the disturbance can also be determined using methods described below.

A signal amplitude at the Mach-Zehnder detector 128 can correspond, at least in part, to a polarization state of light 112 entering the first splitter/coupler 110. As a polarization state of incoming light drifts, output from the Mach-Zehnder detector correspondingly changes. For example, under some polarization states, the output of the Mach-Zehnder sensor can have an unsuitably low signal-to-noise ratio, which can result in so-called "polarization fading" of the output from the Mach-Zehnder detector. It was discovered that such polarization fading can be reduced or eliminated by randomly adjusting a polarization state of incoming light to maintain a suitable signal-to-noise ratio, although the exact polarization state of the incoming beam of light does not matter. Accordingly, it was discovered that the polarization state can be randomly varied, allowing the polarization state of the source to extend through a surface of the Poincare Sphere.

In FIG. 3, a sensor 100a includes a polarization scrambler 132 configured to intermittently adjust a polarization state of incoming light 112 to maintain a suitable signal-to-noise ratio at the Mach-Zehnder detector 128. A polarization scrambler has little to no effect on the Michelson portion of the sensor, since the polarization-phase conjugation devices (e.g., Faraday rotation mirrors) conjugate the polarization state of reflected light, effectively undoing any effects that a change in polarization might have as light travels between the splitter 110 and the devices 122a, 122b in the forward path and then from the devices back to the splitter/coupler and the Michelson detector 124.

A suitable polarization scrambler 132 is an electrically driven polarization controller-scrambler of the type produced by Agiltron, model NOPS-115111331. Such a device can be controlled by three or four (e.g., depending on the model) input voltages that can be varied over a suitable voltage range to provide myriad polarization states. In one operative embodiment, different drive signals can be applied to each (e.g., three or four) of the scrambler elements. Each respective drive signal can be selected to allow a large number of polarization states to be swept in a time-varying random manner.

Such random adjustment of polarization is quite different from the active control and matched polarization states of independent beams of light required in sensors of the type disclosed in U.S. Pat. Nos. 7,499,176, 7,499,177 and 6,778,717. Such active control requires a very complex polarization controller scheme and is expensive to implement. In addition, the active polarization control of the prior art requires the sensor to intermittently pause while light having a new, suitable polarization state is counter-propagated subsequent to a detected disturbance. In contrast, little to no delay is needed for the sensor 100a to detect a subsequent disturbance. Accordingly, a sensor 100, 100a can detect a disturbance subsequent to a first (e.g., "diversionary") disturbance and cannot easily be by-passed using such a first disturbance to disrupt the sensor, overcoming a serious, long-felt deficiency of the prior art.

Devices 132 capable of randomly changing the polarization state, as just described, are substantially less expensive than polarization controllers configured to match polarization states of different beams of light, as required by systems disclosed in U.S. Pat. No. 6,778,717. In addition, randomly changing a polarization state of incoming light 112 can occur much more quickly than matching the polarization states of a pair of light beams to each other. Accordingly, hybrid Michelson/Mach-Zehnder systems disclosed herein can more quickly respond to subsequent disturbances than systems that require matched polarization states of different beams of light and can be produced at lower cost than previously proposed sensors.

Paths of Light through Disclosed Interferometer Systems

Referring to FIGS. 2 and 3, the modulation control can emit a highly-coherent beam of light 112 that enters the splitter/coupler 110 that splits the light 112 into a first portion that travels through the first optical conduit 114a and a second portion that travels through the second optical conduit 114b. The light travelling through the first optical conduit 114a enters an optical splitter 116a positioned adjacent the distal end 118 of the first optical conduit, and the light travelling through the second optical conduit 114b enters an optical splitter 116b positioned adjacent the distal end of the second optical conduit. The respective optical splitters 116a, 116b can split the respective beams of light into respective portions that enter the distal coupler 120 and respective portions that impinge on the respective polarization-phase conjugation devices 122a, 122b.

The portions of light that impinge on the devices 122a, 122b are reflected, and each of the devices can conjugate a polarization state of the respective light portions. The reflected light portions can travel through the splitters 116a, 116b, into the respective conduits 114a, 114b and back to the proximal splitter/coupler 110. The reflected portions of light can be recombined at coupler 110 and a portion of the recombined light can illuminate the Michelson detector 124. Light illuminating the Michelson Detector can define an optical signal that is influenced by each of the optical conduits 114a, 114b, including any disturbances to the conduits. Light illuminating the Michelson Detector has passed through the pair of the conduits 114a, 114b twice—once before illuminating the respective polarization-phase conjugation devices and second time after being reflected therefrom and thus can be influenced twice by the same perturbation. The resulting optical signal can provide twice the sensitivity compared to, for example, a Mach-Zehnder or other interferometer in which an optical signal passes but once through a disturbed optical path.

The respective portions that enter the distal coupler 120 can be combined, can pass through the return conduit 126, which imposes a further optical delay (e.g., TL) that typically can equal T1+T2, and can illuminate the Mach-Zehnder detector 128. In contrast to light illuminating the Michelson Detector 124, a major portion (e.g., except for reflections and other "noise") of light illuminating the Mach Zehnder Detector 128 has passed through the pair of the optical conduits 114a, 114b once, and thus has been influenced by a given perturbation once. In contrast, the optical received by the Michelson Detector 124 has been influenced twice by the same disturbance, as described above.

Passive Optical Sensors

In some instances, the first and second optical conduits 114a, 114b can have similar optical properties and similar lengths; in such instances it does not matter which of the conduits is considered the sensing conduit and the reference conduit. In some embodiments, the reference and sensor optical conduits 114a, 114b are physically separate conduits positioned adjacent each other in a "bundle" (also referred to as a "cable"). In other embodiments, the optical conduits 114a, 114b are in physically separate cables.

For example, a conventional fiber optic bundle can include several individual optical fibers (e.g., single-mode fibers) shrouded by one or more outer sheaths. One of the individual optical fibers can define the sensor conduit (e.g., 114a) and another of the individual optical fibers can define the reference conduit (e.g., 114b). Yet another of the individual optical fibers can define the return conduit 126. All fibers defining the conduits 114a, 114b, 126 can be positioned within and shrouded by the common outer sheath(s). Although such optical fibers are positioned relatively close to each other (e.g., within several millimeters, of each other), a physical disturbance (e.g., an impact or perturbation) applied to the outer sheath(s) will be transmitted to each of the individual fibers slightly differently. Moreover, each of the individual fibers can respond (e.g., deform or have their respective refractive indices altered momentarily) to identical loads somewhat differently. Thus, in practice, a disturbance to the cable generally will perturb the reference and the signal conduits 114a, 114b differently.

Since physical responses typically differ between the "sensor" conduit and the "reference" conduit, light travelling through the "sensor" conduit can arrive at a terminal end 118 of the sensor conduit at a slightly different time, and possibly with a different polarization state, than light travelling through the "reference" conduit. Thus, optical signals observed at each respective terminal end will usually be out of phase from each other by a nominal amount. When either or both of the sensor and reference conduits has been disturbed, the relative phase of the optical signals observed at each respective terminal end will tend to shift from the nominal level from the undisturbed conduits. In the case of the Michelson interferometer, having the ability to separate and compare the delay between receiving the first (outbound) of the optical signals and the second (inbound) of the optical signals (e.g., an observed time-shift between the signals), and accounting for characteristics of the interferometer components (e.g., lengths of optical conduits, speed of light through the conduits), the position of a disturbance can be determined. In another approach, the first signal portion observed by the Mach-Zehnder detector can be compared to the extracted first signal portion observed by the Michelson interferometer to provide a measure of the location of the disturbance.

Although many factors can cause an observed phase shift between signals conveyed through the first and second optical conduits, a nominal, or baseline, phase shift between observed signals of undisturbed reference and sensor conduits can be determined. Thus, one can infer that a sensor cable (e.g., a bundle having a sensor conduit and a reference conduit) has been disturbed when a sufficiently large (or a threshold) deviation from a baseline phase shift is observed. In addition, observing such a phase-shift at more than one location in the total optical path (e.g., outbound and inbound signals), combined with characteristics of the sensor cable (e.g., its length, the speed at which light travels through each of the optical conduits), a location of the disturbance can be inferred.

In some embodiments, the third, insensitive conduit 126, which imposes a further signal time delay of TL for the Mach Zehnder interferometer, can be positioned adjacent one or both of the sensor conduit (e.g., conduit 114a) and the reference conduit (e.g., conduit 114b). For example, an optical cable can have a plurality of optical conduits within a common sheath(s), as described above. One of the optical conduits can form the insensitive conduit 126 configured to return light to the Mach-Zehnder detector 128, and the other two conduits can form the sensor conduit and the reference conduit, respectively. In such an embodiment, the reference and sensor conduits can be passively terminated adjacent a distal end 118 of the optical cable, as shown in FIGS. 2 and 3.

For example, respective splitters 116a, 116b and polarization-phase conjugation devices 122a, 122b, and the distal coupler 120 can be positioned adjacent a distal end 118 of the optical cable 130. Such a configuration can provide an entirely passive sensor to extend for a distance of up to, for example, about 65 km, from active components (e.g., the light source, the Michelson detector, the Mach-Zehnder detector, a computing environment, etc.).

In some embodiments (described more fully below), a second passive sensor can extend in an opposite direction from a first passive sensor for a distance of up to, for example, about 65 km. In such embodiments, a sensor system can extend up to, for example, about 130 km, with the active components 132a, 132b being positioned at about a midpoint of the sensor system.

Multiplexed Phase Generated Carrier with Homodyne Demodulation

Modulation of current to a laser (e.g., a diode laser) can affect both amplitude and wavelength (optical frequency) of emitted light. Either effect (amplitude or wavelength) can be used to drive a sensor as disclosed herein. For example, if the sensor conduit and reference conduit are substantially identical, amplitude modulation effects can dominate the sensor's response. On the other hand, if one of the conduits is shorter than the other by, for example, a few meters, then frequency modulation effects may dominate the sensor's response. Sensors described herein can use either approach.

For simplicity and brevity, frequency modulation effects (and thus methods relating to interferometers with different-length sensor and reference conduits) are fully described. Nonetheless, those of ordinary skill will appreciate similar methods for obtaining disturbance and position information using interferometers with equal-length sensor and reference conduits, and the corresponding amplitude modulation. The following methods can be implemented in a computing environment, as disclosed more fully below.

Examples of Innovative Methods Related to Detecting a Disturbance and its Location A Michelson sensor portion can provide an optical signal having two information components. One component (I) can contain information obtained from a disturbance as light travels from a light source (proximal end) to a polarization-phase conjugation devices (distal end). A second component (II) can contain information obtained as the light propagates back from the distal end to the proximal end. The Mach Zehnder sensor portion can provide an optical signal having one information component, namely information obtained from the disturbance as light travels from the source (proximal end) to the coupler (distal end). As an approximation, the response of the Mach Zehnder sensor portion can be assumed to be identical to the first component (I) of the Michelson sensor portion's response, particularly if they share the same optical conduits, and can be used in a transformation to isolate the second component (II) from the Michelson Interferometer response. A time delay between the first (I) and second (II) responses can provide a measure of the location of the disturbance along the length of the sensor. Such a transformation is now described.

The Michelson sensor portion's response (MI) can be described by a phasor, e.g., its in-phase (I) and quadrature (Q) response components.

$$I_{MI}(t) = MI \cos[\phi(t-T2-TL) + \phi(t+T2-TL)] \quad (1)$$

$$Q_{MI}(t) = MI \sin[\phi(t-T2-TL) + \phi(t+T2-TL)] \quad (2)$$

where TL=T1+T2.

The first (I) and second (II) components of the Michelson Interferometer are the first and second phase angle terms in each of Equations (1) and (2).

The Mach Zehnder sensor portion's response (MZ) can also be described by its phasor components, I and Q.

$$I_{MZ}(t) = MZ \cos[\phi(t-T2)] \quad (3)$$

$$Q_{MZ}(t) = MZ \sin[\phi(t-T2)] \quad (4)$$

Since both the Michelson sensor portion and the Mach Zehnder sensor portion share the same sensor and reference conduits (e.g., conduits 114a, 114b in FIGS. 2 and 3), each sensor portion "sees" the same disturbance. Generally, the Mach Zehnder response is delayed because the Mach-Zehnder sensor portion includes the insensitive conduit 126 that returns the Mach-Zehnder's optical signal to the Mach-Zehnder detector 128. Mathematically, this delay can be represented as TL. Shifting the Michelson sensor portion's response in equations (1) and (2) by the cable delay TL, Equations (5) and (6) are arrived at:

$$I_{MI}(t+TL) = MI \cos[\phi(t-T2) + \phi(t+T2)] \quad (5)$$

$$Q_{MI}(t+TL) = MI \sin[\phi(t-T2) + \phi(t+T2)] \quad (6)$$

The first (I) components of equations (5) and (6) have the same timing as the components of the Mach Zehnder response in equations (3) and (4), as expected since the outbound light travels the same path for the first component (I) in the Michelson sensor portion and the Mach-Zehnder sensor portion. Equations (5) and (6) can then be rearranged using trigonometric identities to arrive at:

$$I_{MI}(t+TL) = MI\{\cos[\phi(t-T2)]\cos[\phi(t+T2)] - \sin[\phi(t-T2)]\sin[\phi(t+T2)]\} \quad (7)$$

$$Q_{MI}(t+TL) = MI\{\sin[\phi(t-T2)]\cos[\phi(t+T2)] - \cos[\phi(t-T2)]\sin[\phi(t+T2)]\} \quad (8)$$

Substituting the Mach Zehnder responses shown in Equations (3) and (4) into equations (7) and (8), Equations (9) and (10) are obtained:

$$I_{MI}(t+TL) = \frac{MI}{MZ}\{I_{MZ}(t)\cos[\phi(t+T2)] - Q_{MZ}(t)\sin[\phi(t+T2)]\} \quad (9)$$

$$Q_{MI}(t+TL) = \frac{MI}{MZ}\{Q_{MZ}(t)\cos[\phi(t+T2)] + I_{MZ}(t)\sin[\phi(t+T2)]\} \quad (10)$$

An "X" response can be defined as $$I_X(t) = \frac{MI}{MZ}\cos[\phi(t+T2)] \quad (11)$$

$$Q_X(t) = \frac{MI}{MZ}\sin[\phi(t+T2)] \quad (12)$$

Substituting equations (11) and (12) into (9) and (10), equations (13) and (14) are obtained:

$$I_{MI}(t+TL) = I_{MZ}(t)I_X(t) - Q_{MZ}(t)Q_X(t) \quad (13)$$

$$Q_{MI}(t+TL) = Q_{MZ}(t)I_X(t) + I_{MZ}(t)Q_X(t) \quad (14)$$

Solving equations (13) and (14) for $I_X(t)$ and $Q_X(t)$, equations (15) and (16) are obtained $$I_X(t) = \frac{1}{MZ^2}\{I_{MZ}(t)I_{MI}(t+TL) + Q_{MZ}(t)Q_{MI}(t+TL)\} \quad (15)$$

$$Q_X(t) = \frac{1}{MZ^2}\{I_{MZ}(t)Q_{MI}(t+TL) - Q_{MZ}(t)I_{MI}(t+TL)\} \quad (16)$$

Figure 4:
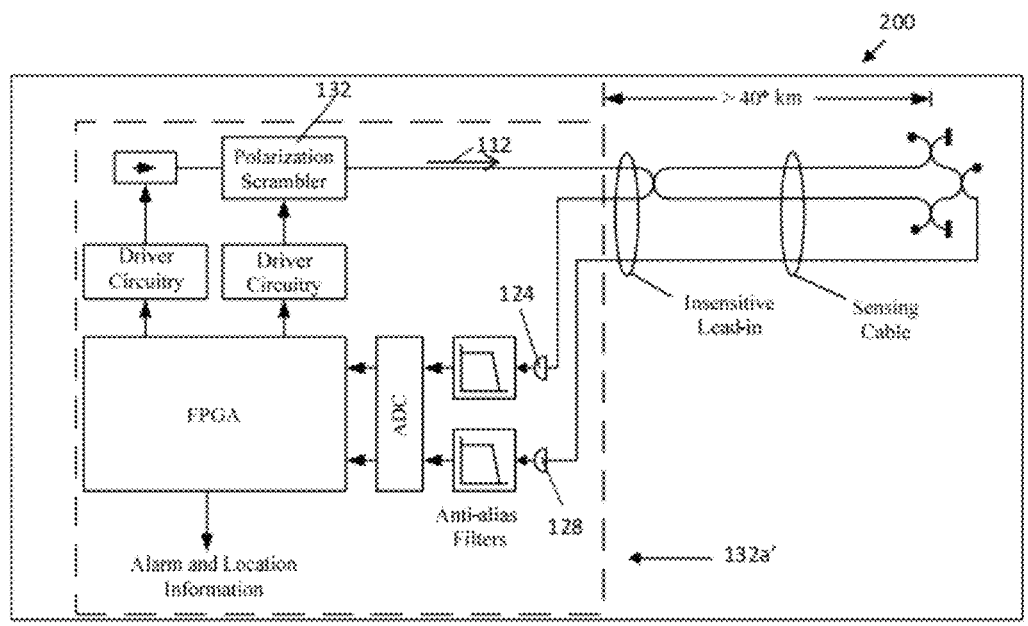
FIG. 4 shows aspects of an innovative disturbance detector as disclosed herein.

The equations derived in the foregoing are based on continuous functions of time. Nonetheless, the detector 124, 128 outputs and these equations can be digitized and converted to the sample data equivalents using known approaches. Thus, the equations just described can be implemented in a digital computing environment. A digital embodiment 200 of the system 100a shown in FIG. 3 is illustrated in FIG. 4.

Before comparing the respective Mach-Zehnder and Michelson signals, the Michelson data can be mathematically delayed by a fixed amount corresponding to, for example, the sensor length (TL). Such an introduced delay can be used to address the differences between the Mach-Zehnder and Michelson interferometer configurations.

Sampling and Modulation

In one embodiment, a sample frequency of fs=10 MHz (sample period of Ts=0.1 microseconds) can be used. A relative speed of an optical signal (compared to the speed of light in a vacuum) of 68.13% corresponds to 10.36 meters per sample period. Based on this sample rate, a 1 km sensor can have a delay line with 97 taps. For computational ease, 100 taps per km of sensor are assumed (e.g., a 20 km sensor would require a 2000 tap delay line).

A proposed modulation frequency is $$fm=fs/8=1.25 \text{ MHz} \quad (17)$$

This can become the carrier frequency associated with an in-Phase (I) component and the carrier for the Quadrature (Q) component can be at the second harmonic:

$$2fm=fs/4=2.5 \text{ MHz} \quad (18)$$

Figure 5:
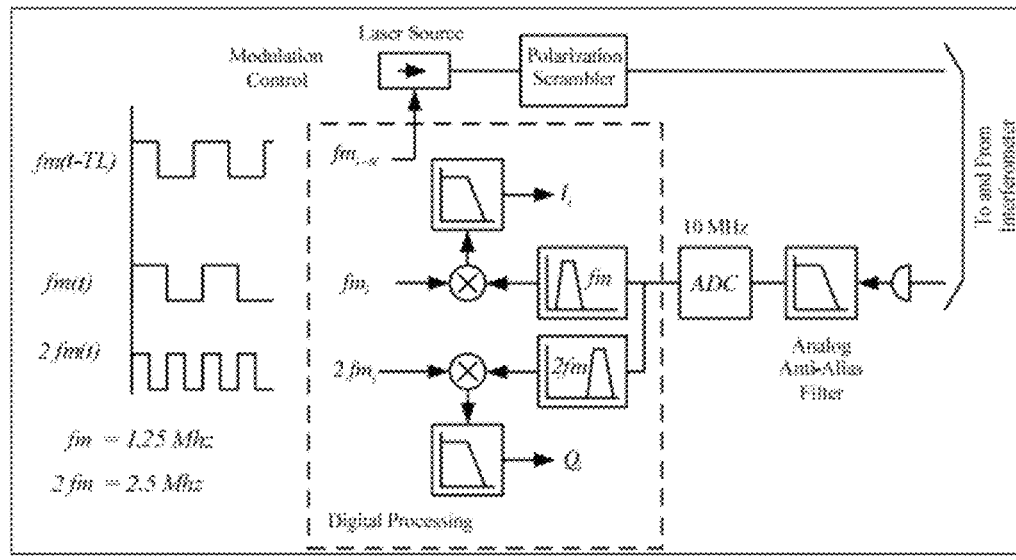
FIG. 5 shows aspects of a digital processor configured for use with a disturbance detector as shown in FIG. 4.

With a sample frequency of 10 MHz, this can provide ample room for an analog anti-alias filter after the detector and before the ADC. A representative sampling and modulation timing diagram for each detector is illustrated in FIG. 5.

A frequency fu can denote an upper frequency content of the response. In some instances, fu can be about 700 kHz. In a working embodiment in a laboratory environment, the highest frequency observed to date with the lab system is about 400 kHz for a Michelson sensor portion and about 200 kHz for a Mach Zehnder sensor portion. In many instances, the Michelson sensor portion's response frequency is less than about 200 kHz.

The modulation drive signal can be advanced (e.g., by TL) from a demodulation signal to account for time delay arising from the length of the interferometer. A magnitude of the advance can be reduced by a delay between the Mach Zehnder coupler and the Mach Zehnder detector.

Sensor performance can correspond, in some instances, to the performance of the analog anti-aliasing filter. For example, the modulation scheme described above can cause a detector output rich in harmonics.

Locating a Disturbance from Observed Phase- or Time-Shift

A working embodiment of a phase integration approach to determining the position of a disturbance is described. Under this approach, a time difference between output of the Michelson sensor portion and the Mach Zehnder sensor portion arising from physical deformation of the optical conduits is determined. As indicated by the equations above, such a phase shift can correspond to the position of the disturbance along a sensitive portion of a hybrid Michelson and Mach Zehnder sensor 100, 100a, as shown in FIGS. 2 and 3. Such an innovative approach overcomes many deficiencies (and the concomitant performance limitations) of prior art sensors (e.g., coaxial cable, electric field or acoustic cable).

Figure 6:
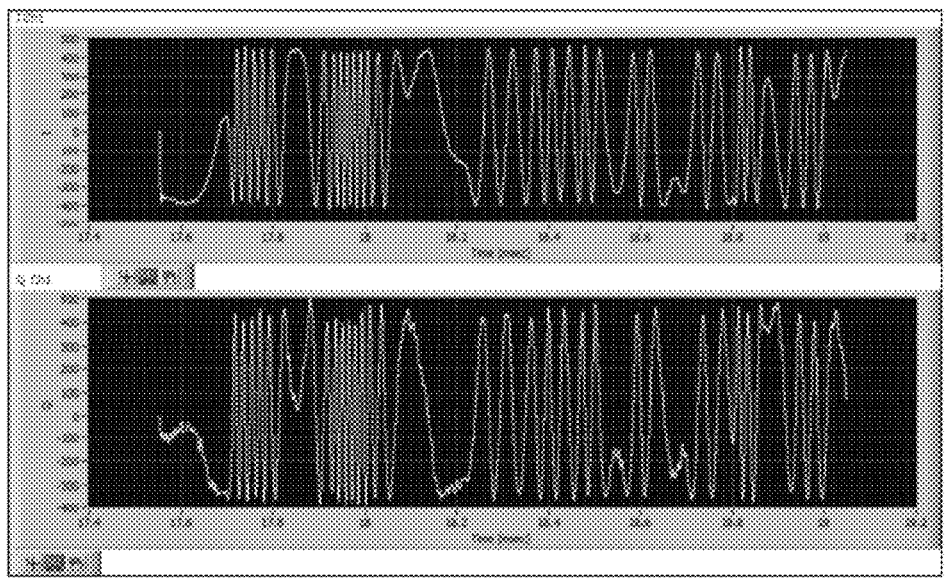
FIG. 6 shows a plot of two time-varying components of a first phasor output from a working embodiment of an innovative interferometer of the type disclosed herein.
Figure 7:
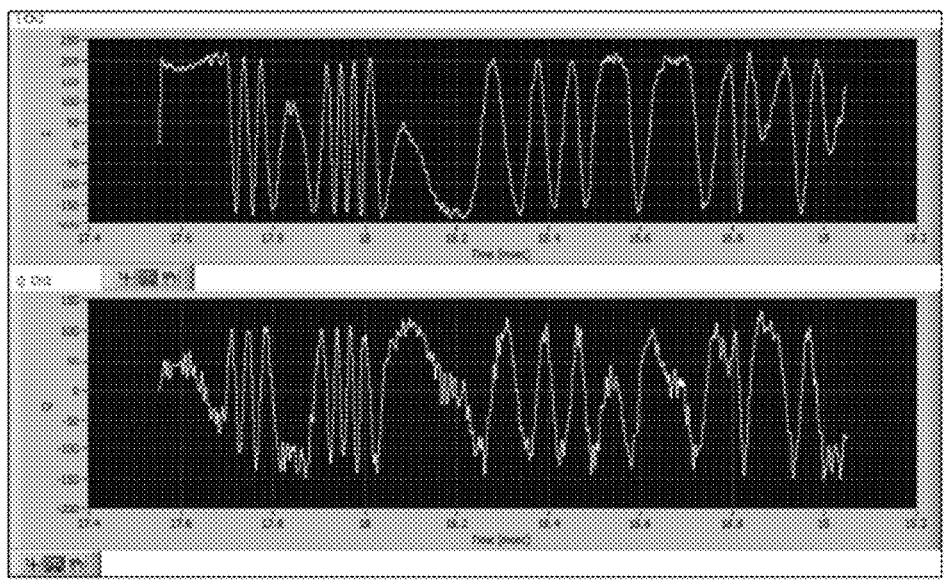
FIG. 7 shows a plot of two time-varying components of a second phasor output from the working embodiment of an innovative interferometer of the type disclosed herein.

The phasor output I and Q responses shown in FIG. 6 for the Michelson sensor portion and FIG. 7 for the Mach Zehnder sensor portion are represented by equations (1), (2), (3), and (4), respectively.

An integration of the incremental phase measurements for each of the respective interferometers, over a short period of time, such as, for example, about 10-20 milliseconds, can provide a measure of a change in length of the optical conduits 114a, 114b relative to each other over the selected integration time for each of the interferometers. Since both interferometers share the same optical conduits, the integrated incremental phase measurements for each of the respective interferometers should be the same, but shifted in time in accordance with the position of the disturbance. Results of such an integration are shown in FIG. 8, showing a similar integrated phase pattern between the two interferometers, as well as a time delay between the signals that can be used to determine the position of the disturbance.

Figure 8:
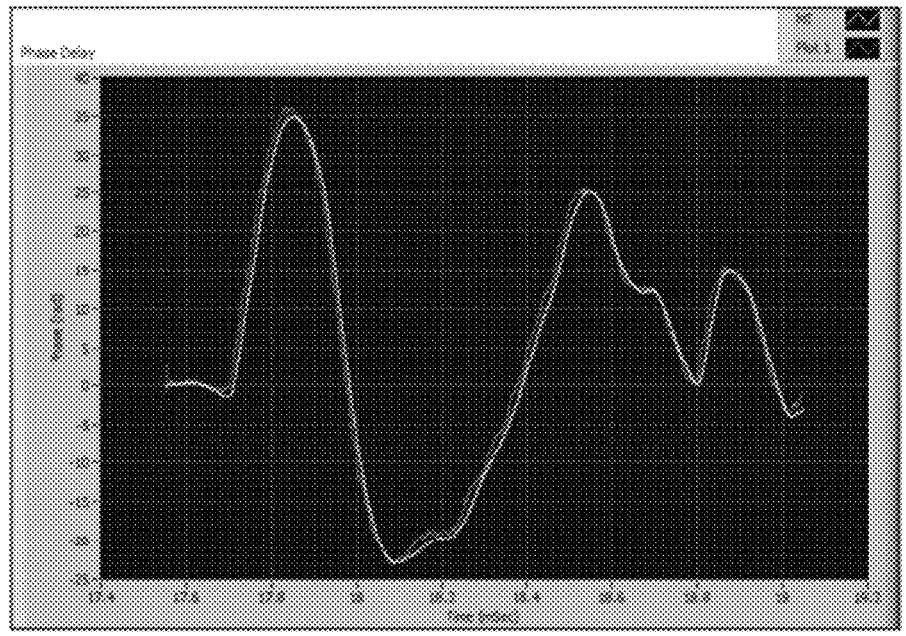
FIG. 8 shows a plot of a time-varying total phase shift for each of the first and the second phasor outputs.

In FIG. 8, the vertical axis represents phase angle in radians. For example, a response range of between about −24 to about +35 radians can correspond to about 9.4 cycles (fringes), corresponding to about 14.57 micrometers change in relative length of the sensor conduit and the reference conduit, assuming a light source having a wavelength of 1,550 nanometers is used in an example embodiment. In this example, the 9.4 cycle response can occur during a period of about 0.25 milliseconds, representing an average frequency response of about 37.6 kHz. The shift in time between the responses provides a measure of the location of the underlying disturbance to the sensitive portion of the hybrid interferometer.

To determine the position of the disturbance location, one integrated phase return can be continually subtracted from the other integrated phase return with different time shifts, and a least squares fit of the resulting data can be computed. Such an approach can yield a generally "V" shaped correlation curve, with the inferred location of the disturbance being positioned at the apex of the "V".

In determining the position of a disturbance, one of the displacement profiles can be subtracted from the other with the different delay parameters as outlined above to find a best fit. In one working embodiment, the two responses were displaced by between about 0 to about 2000 sample points. At a 10 MHz sample rate, the range bin accuracy was approximately 10 meters. This can be improved upon by interpolating the location of the apex of the "V".

The equations presented above and in this section are summarized in sample data (e.g., digitized) form in the following section. The digitized form can be used in computer implementable methods.

Determining a Disturbance Type from Observed Signals

An optical signal can carry information related to the type of disturbance that has occurred. In some instances, an observed optical signal (e.g., a signal with a phase-shift, a change in amplitude, or both), can correspond to a given type of disturbance (e.g., a leak in a pipeline, an act of digging underground, a cut fence). Knowing how an optical signal from a sensor varies in response to different disturbances can allow a user to determine what type of disturbance has occurred based on, at least in part, comparing an observed signal to another observed signal generated in response to a known disturbance.

For example, a given disturbance can excite a given environment in a substantially identical manner each time the disturbance occurs, thereby resulting in a substantially identical perturbation to a given sensor each time the disturbance occurs. When a sensor is perturbed in a given manner, it can physically respond (e.g., undergo a strain or other deformation) in a corresponding manner, and thereby modify an optical signal in a corresponding manner.

In some instances, a sensor can be calibrated against different disturbances by recording each observed optical signal arising from each of a variety of different disturbances. For example, a "look up" table of signals corresponding to each disturbance can be generated. A subsequent observed optical signal (e.g., arising from an unknown disturbance type) can be compared to each of the recorded observed optical signals, and a corresponding disturbance type can be inferred when the observed optical signal suitably matches a previously recorded optical signal.

As noted above, a sensor can be excited (and thus can respond) differently in one environment compared to another environment. In some instances, a sensor calibration (e.g., generation of a "look-up" table) can be completed after the sensor has been installed.

Digitized Equations for Determining a Position of a Disturbance

The equations presented above are expressed in their continuous time form. Nonetheless, the analysis presented above can be performed digitally. Accordingly, the equations are presented here in digitized form.

The observed (e.g., measured) parameters are the Michelson and Mach Zehnder phasors $\{I_{MIi}, Q_{MIi}\}$ and $\{I_{MZi}, Q_{MZi}\}$ taken at instant "i". From the measured parameters $\{I_{Xi}, Q_{Xi}\}$ can be determined using:

$$I_{Xi} = \{I_{MZi}I_{MI(i+M)} + Q_{MZi}Q_{MI(i+M)}\} \tag{19}$$

$$Q_{Xi} = \{I_{MZi}Q_{MI(i+M)} - Q_{MZi}I_{MI(i+M)}\} \tag{20}$$

The indexing constant, M, relates to the number of samples corresponding to the time delay TL. Note: the MZ terms in equations (15) and (16) are ignored since they cancel when computing the small angle tangent approximation.

The Mach Zehnder response $\{I_{MZi}, Q_{MZi}\}$ can be used to compute the Mach Zehnder incremental angle using $$\delta\phi_{MZi} = \frac{Q_{MZi}I_{MZ(i-1)} - I_{MZi}Q_{MZ(i-1)}}{I_{MZi}I_{MZ(i-1)} + Q_{MZi}Q_{MZ(i-1)}} \tag{21}$$

and the derived "X" response $\{I_{Xi}, Q_{Xi}\}$ can be used to compute the incremental "X" angle using $$\delta\phi_{XZi} = \frac{Q_{Xi}I_{X(i-1)} - I_{Xi}Q_{X(i-1)}}{I_{Xi}I_{X(i-1)} + Q_{Xi}Q_{X(i-1)}} \tag{22}$$

When a disturbance is detected (e.g., a threshold is exceeded), the two displacement profiles can be computed $$\phi_{MZj} = \delta\phi_{MZj} + \phi_{MZ(j-1)}, j=0,1,2\ldots N \tag{23}$$

$$\phi_{Xj} = \delta\phi_{Xj} + \phi_{X(j-1)}, j=0,1,2\ldots N \tag{24}$$

The resulting displacement profiles can be correlated in time to determine the location of the disturbance.

Computing Environments

Figure 9:
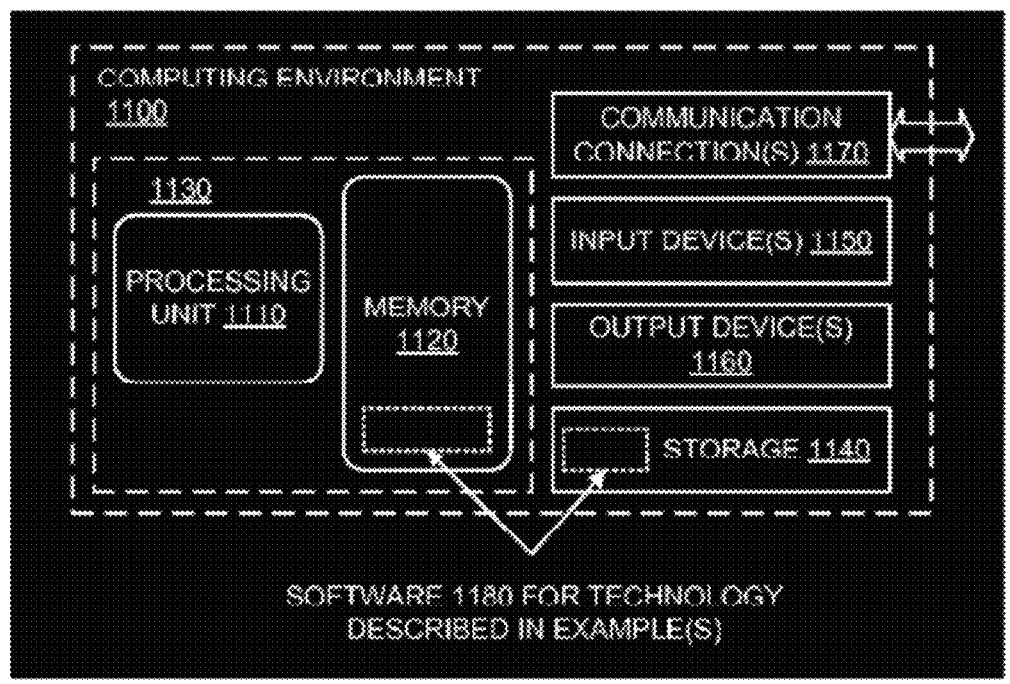
FIG. 9 shows a block diagram of a computing environment as disclosed herein.

FIG. 9 illustrates a generalized example of a suitable computing environment 1100 in which described methods, embodiments, techniques, and technologies may be implemented. The computing environment 1100 is not intended to suggest any limitation as to scope of use or functionality of the technology, as the technology may be implemented in diverse general-purpose or special-purpose computing environments. For example, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 9, the computing environment 1100 includes at least one central processing unit 1110 and memory 1120. In FIG. 9, this most basic configuration 1130 is included within a dashed line. The central processing unit 1110 executes computer-executable instructions and may be a real or a virtual processor. In a multi-processing system, multiple processing units execute computer-executable instructions to increase processing power and as such, multiple processors can be running simultaneously. The memory 1120 may be volatile memory (e.g., registers, cache, RAM), non-volatile memory (e.g., ROM, EEPROM, flash memory, etc.), or some combination of the two. The memory 1120 stores software 1180 that can, for example, implement one or more of the innovative technologies described herein. A computing environment may have additional features. For example, the computing environment 1100 includes storage 1140, one or more input devices 1150, one or more output devices 1160, and one or more communication connections 1170. An interconnection mechanism (not shown) such as a bus, a controller, or a network, interconnects the components of the computing environment 1100. Typically, operating system software (not shown) provides an operating environment for other software executing in the computing environment 1100, and coordinates activities of the components of the computing environment 1100.

The storage 1140 may be removable or non-removable, and includes magnetic disks, magnetic tapes or cassettes, CD-ROMs, CD-RWs, DVDs, or any other medium which can be used to store information and which can be accessed within the computing environment 1100. The storage 1140 stores instructions for the software 1180, which can implement technologies described herein.

The input device(s) 1150 may be a touch input device, such as a keyboard, keypad, mouse, pen, or trackball, a voice input device, a scanning device, or another device, that provides input to the computing environment 1100. For audio, the input device(s) 1150 may be a sound card or similar device that accepts audio input in analog or digital form, or a CD-ROM reader that provides audio samples to the computing environment 1100. The output device(s) 1160 may be a display, printer, speaker, CD-writer, or another device that provides output from the computing environment 1100.

The communication connection(s) 1170 enable communication over a communication medium (e.g., a connecting network) to another computing entity. The communication medium conveys information such as computer-executable instructions, compressed graphics information, or other data in a modulated data signal.

Computer-readable media are any available media that can be accessed within a computing environment 1100. By way of example, and not limitation, with the computing environment 1100, computer-readable media include memory 1120, storage 1140, communication media (not shown), and combinations of any of the above.

Other Embodiments

Using the principles disclosed herein, those of ordinary skill will appreciate a wide variety of possible embodiments of interferometer systems, particularly those configured to detect a disturbance. For example, a disturbance can be detected from observing polarization separation, wavelength separation, or both, in addition to or instead of modulation separation.

Modulation Separation with a Plurality of Light Sources

Figure 10:
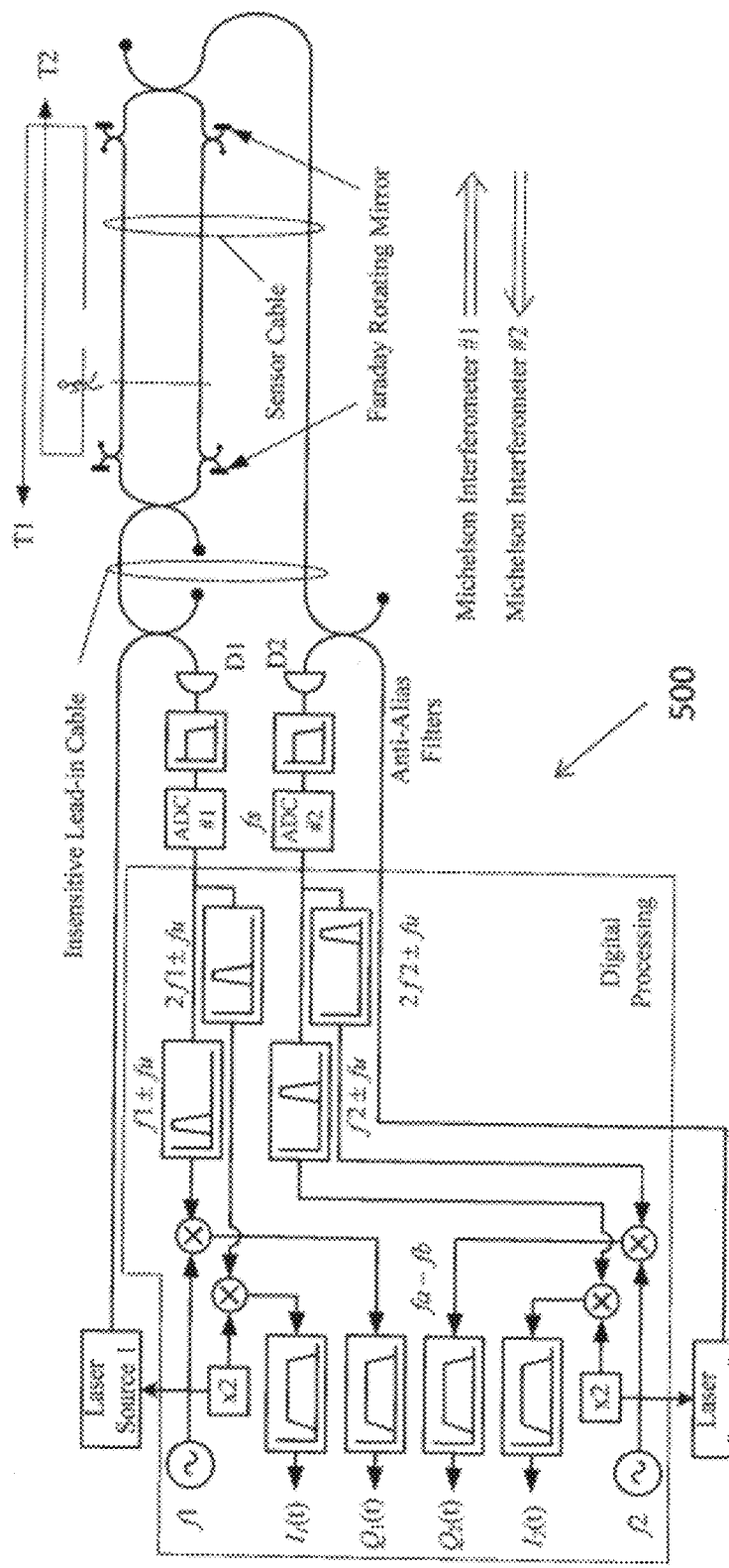
FIG. 10 shows aspects of an alternative system configured to use a first and second light sources and modulation separation to detect the presence and location of a disturbance.

Although innovative interferometer systems 100, 100a, 200 comprising a single light source have been described above, plural light sources can be used in a system 500, as shown, for example, in FIG. 10. For example, respective amplitudes of first and second light sources (respectively labeled "Laser Source 1" and "Laser Source 2" in FIG. 10) can be modulated at respective first and second frequencies. The output of each detector D1, D2 can be demodulated to derive the respective interferometer responses. As shown in FIG. 10, such a system can include two polarization phase conjugation devices (labeled as "Faraday Rotating Mirror" in FIG. 10) corresponding to each optical conduit of the interferometer.

In such a system 500, the first and second modulation frequencies are preferably well above a target response band of frequencies to achieve a suitable sensitivity to disturbances. For example, modulation frequencies can range between about 50 kHz to 750 kHz. In this example, it is suggested to use modulation frequencies of 20 MHz and 30 MHz. Such a selection of frequencies allows the respective responses to be clearly distinguishable and separable. As indicated in FIG. 10, a mixer can be used to drop the respective responses to a baseband before filtering with a suitable low pass filter.

In FIG. 10, Laser Source #1 can be modulated at a first frequency f1. The modulated output of Laser #1 can be coupled to the lead-in cable and the Michelson Interferometer #1. The response from this interferometer measured at the detector, D1, can be operatively coupled to the processor.

Laser Source #2 can be modulated at a second frequency f2. The modulated output of Laser #2 can be coupled to the lead-in cable and the Michelson Interferometer #2. The response from this interferometer measured at the detector, D2, can be operatively coupled to the processor.

For example, the respective output of each detector, D1 and D2, can pass through anti-alias filters to remove high frequency components such that the outputs of the Analog to Digital Converts (ADC #1 and #2) faithfully represent the desired analog output of the detectors. The sampling rate of the ADC converters can be fs. The corner frequency of the anti-alias can be less than about half the sample frequency to be consistent with the Nyquist sampling criteria.

In processing the digital signal, the outputs of the detectors can pass through band-pass filters about the modulating frequencies. Such filters can remove unwanted terms (e.g., unwanted cross-products that can arise in mixing) before mixing. The bandwidth of each of the filters can be twice the upper response frequency (i.e.: 2fu). Such filters tend to remove the baseband components from the detection process, leaving only the modulation frequencies used during demodulation, e.g., $\omega_1$ and $\omega_2$ terms, and double these frequencies.

The signals can be demodulated by multiplying with suitable modulation frequencies (e.g., by multiplying by +1, and −1 at suitable modulation rates; f1, 2f1, f2 and 2f2). This translates the responses down to baseband where they are band pass filtered to obtain the desired phasor outputs $[I_1(t), Q_1(t)]$ and $[I_2(t), Q_2(t)]$.

Interpreting the I and Q Responses

The response from the interferometer shown in FIG. 10 (or in FIGS. 2 and 3) can appear as a rotating vector that traces out a circle, as shown in FIGS. 11(A) and 11(B).

A direction of rotation can be determined by the relative change in length of the sensor conduit and the reference conduit. In general, the response can be expected to rotate one direction for a number of cycles under the influence of a disturbance and to rotate in an opposite direction as the conduits return to their respective undisturbed condition.

Since a response typically contains many different frequency components, the direction of rotation may appear constant, although its angular speed can vary considerably with time. The resulting pattern is generally unique to each disturbance, but is generally observed to be the same from both detectors since both detectors are receiving signals from the same fibers responding to the same disturbance. Nonetheless, the detectors receive the optical signals at different times, since the respective path lengths differ for the two interferometers. Accordingly, the position of the disturbance target can be identified by correlating response #1 with the response #2.

As noted above, each disturbance to the sensitive conduits creates a unique response in terms of the number of cycles.

The table shown in FIG. 12 identifies several acts that together form an innovative method as disclosed herein. For example, referring to the systems shown in FIGS. 2 and 3, and the table in FIG. 12, light can be launched into a fiber 1201. The light can be split into a first outbound portion and a second outbound portion 1202. The first outbound portion can be split into a first reflection portion and a corresponding first coupling portion 1203. The second outbound portion can be split into a second reflection portion and a corresponding second coupling portion 1204. The first reflection portion can be reflected with a first polarization-phase conjugation device and the second portion can be reflected with a second polarization-phase conjugation device 1205. The first reflection portion and the second reflection portion can be combined 1206. The first coupling portion and the second coupling portion can be combined 1207.

The table shown in FIG. 13 identifies several acts that together form another innovative method as disclosed herein. For example, referring the systems shown in FIGS. 2 and 3, and the table shown in FIG. 13, light can be launched into a fiber-optic sensor comprising a Michelson sensor portion, a Mach-Zehnder sensor portion, and an operative coupling therebetween. A combined first signal portion and second signal portion can be detected from the Michelson sensor portion 1301. The first signal portion can be detected from the Mach-Zehnder sensor portion 1202. The location of a disturbance can be sensed based on, at least in part, a comparison of the first signal portion and the second signal portion 1304.

Disclosed Principles are Not Limited to Described Embodiments

This disclosure makes reference to the accompanying drawings which form a part hereof, wherein like numerals designate like parts throughout. The drawings illustrate specific embodiments, but other embodiments may be formed and structural changes may be made without departing from the intended scope of this disclosure. Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. These terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" as well as "and" and "or."

Accordingly, this detailed description shall not be construed in a limiting sense, and following a review of this disclosure, those of ordinary skill in the art will appreciate the wide variety of interferometer systems that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope. And, although detailed claims have not been presented here since claims are not a necessary component for a provisional patent application, I reserve the right to claim as my invention all that comes within the scope and spirit of the subject matter disclosed herein, including but not limited to all that comes within the scope and spirit of the following paragraphs.

The invention claimed is:

1. A method of detecting a disturbance using a passively terminated fiber optic sensor, the method comprising:

launching light into a fiber-optic sensor comprising (i) a first fiber portion and a second fiber portion defining a sensitive portion of the sensor, and a third fiber portion defining an insensitive portion of the sensor, each of the first, second and third fiber portions extending between respective proximal and distal ends, (ii) a first splitter-coupler positioned adjacent the proximal ends of the first fiber portion and the second fiber portion and configured to split incoming light between the first fiber portion and the second fiber portion via a third fiber coupler, (iii) a first coupler and second coupler position adjacent the respective distal ends of the first fiber portion and the second fiber portion and configured to combine light from the first fiber portion with light from the second fiber portion and to direct the combined light into the third fiber portion, and (iv) a first polarization-phase conjugation device configured to conjugate a polarization phase of incident light corresponding to the first fiber portion and a second polarization-phase conjugation device configured to conjugate a polarization phase of incident light corresponding to the second fiber portion;

detecting with a first detector a combined first signal portion and a second signal portion from light reflected by the first polarization-phase conjugation device and light reflected by the second polarization-phase conjugation device;

detecting with a second detector the combined first signal portion from light combined by the third fiber coupler and directed into the third fiber portion; and determining the location of a disturbance based on, at least in part, a comparison of the first signal portion and the second signal portion.

2. The method of claim 1, wherein the act of determining the location of a disturbance comprises subtracting the first signal portion from the combined first signal portion and second signal portion.

3. The method of claim 1, further comprising determining a magnitude of the disturbance based in part on a phase shift detected by the first detector, the second detector, or both.

4. The method of claim 3, wherein the act of determining a magnitude of the disturbance comprises the act of counting fringes.

5. The method of claim 4, wherein the act of determining a magnitude of the disturbance further comprises integrating the phase shift and averaging a magnitude of the disturbance determined from the act of counting fringes with a magnitude of the disturbance determined from integrating the phase shift.

6. The method of claim 3, wherein the act of determining a magnitude of the disturbance comprises integrating the phase shift.

7. A non-transitory computer-readable medium containing executable instructions that, when executed, cause an apparatus to perform a method comprising:

launching light into a fiber-optic sensor comprising (i) a first fiber portion and a second fiber portion defining a sensitive portion of the sensor, and a third fiber portion defining an insensitive portion of the sensor, each of the first, second and third fiber portions extending between respective proximal and distal ends, (ii) a first splitter-coupler positioned adjacent the proximal ends of the first fiber portion and the second fiber portion and configured to split incoming light between the first fiber portion and the second fiber portion, (iii) a first coupler and a second coupler positioned adjacent the respective distal ends of the first fiber portion and the second fiber portion and configured to combine light from the first fiber portion with light from the second fiber portion and to direct the combined light into the third fiber portion via a third fiber coupler, and (iv) a first polarization-phase conjugation device configured to conjugate a polarization phase of incident light corresponding to the first fiber portion and a second polarization-phase conjugation device configured to conjugate a polarization phase of incident light corresponding to the second fiber portion;

detecting with a first detector a combined first signal portion and a second signal portion from light reflected by the first polarization-phase conjugation device and light reflected by the second polarization-phase conjugation device;

detecting with a second detector the combined first signal portion from light combined by the third fiber coupler and directed into the third fiber portion; and determining the location of a disturbance based on, at least in part, a comparison of the first signal portion and the second signal portion.

8. The non-transitory computer-readable medium of claim 7, wherein the act of determining the location of the disturbance comprises subtracting the first signal portion from the combined first signal portion and second signal portion.

9. The non-transitory computer-readable medium of claim 7, wherein the method further comprises determining a magnitude of the disturbance based in part on a phase shift detected by the first detector, the second detector, or both.

10. The non-transitory computer-readable medium of claim 9, wherein the act of determining a magnitude of the disturbance comprises the act of counting fringes.

11. The non-transitory computer-readable medium of claim 10, wherein the act of determining a magnitude of the disturbance further comprises integrating the phase shift and averaging a magnitude of the disturbance determined from the act of counting fringes with a magnitude of the disturbance determined from integrating the phase shift.

12. The non-transitory computer-readable medium of claim 9, wherein the act of determining a magnitude of the disturbance comprises integrating the phase shift.

13. A method of constructing a fiber-optic sensor, method comprising:

providing a first fiber portion and a second fiber portion defining a sensitive sensor portion;

providing a third fiber portion defining an insensitive sensor portion, wherein each of the first, second and third fiber portions extend between respective proximal and distal ends; and operatively coupling a first splitter-coupler to the proximal ends of the first fiber portion and the second fiber portion such that the first splitter-coupler is configured to split incoming light between the first fiber portion and the second fiber portion operatively coupling a first coupler and second coupler to the respective distal ends of the first fiber portion and the second fiber portion such that the coupler is configured to combine light from the first fiber portion with light from the second fiber portion and to direct the combined light into the third fiber portion via a third fiber coupler;

providing a first polarization-phase conjugation device configured to conjugate a polarization phase of incident light corresponding to the first fiber portion and a second polarization-phase conjugation device configured to conjugate a polarization phase of incident light corresponding to the second fiber portion, such that the fiber-optic sensor is configured to provide a first signal portion from light combined by the third coupler and directed into the third fiber portion and the fiber-optic sensor is further configured to provide the first signal portion in combination with a second signal portion from light reflected by the first polarization-phase conjugation device and light reflected by the second polarization-phase conjugation device, wherein the first signal and the combined first and second signals are used to estimate a location of a disturbance to the sensitive portion of the sensor.

14. A monitored installation with a passively terminated fiber optic sensor, the monitored installation comprising:

a fiber-optic sensor to receive light, the fiber-optic sensor comprising (i) a first fiber portion and a second fiber portion defining a sensitive portion of the sensor, and a third fiber portion defining an insensitive portion of the sensor, each of the first, second and third fiber portions extending between respective proximal and distal ends, (ii) a first splitter-coupler positioned adjacent the proximal ends of the first fiber portion and the second fiber portion and configured to split incoming light between the first fiber portion and the second fiber portion, (iii) a first coupler and a second coupler positioned adjacent the respective distal ends of the first fiber portion and the second fiber portion and configured to combine light from the first fiber portion with light from the second fiber portion and to direct the combined light into the third fiber portion via a third fiber coupler, and (iv) a first polarization-phase conjugation device configured to conjugate a polarization phase of incident light corresponding to the first fiber portion and a second polarization-phase conjugation device configured to conjugate a polarization phase of incident light corresponding to the second fiber portion;

a first detector configured to detect a combined first signal portion and a second signal portion from light reflected by the first polarization-phase conjugation device and light reflected by the second polarization-phase conjugation device;

a second detector configured to detect the combined first signal portion from light combined by the third fiber coupler and directed into the third fiber portion; and a central processing unit (CPU) configured to determine the location of a disturbance based on, at least in part, a comparison of the first signal portion and the second signal portion.

15. The installation of claim 14, wherein the monitor region comprises one or more of a fence, a pipeline, a rail line, a communication line, a conveyor, a structure affixed to the Earth, and a perimeter.

16. The installation of claim 14, wherein the passively terminated sensitive optical sensor extends away from the active portion between about 1 km and about 65 km.

17. The installation of claim 14, further comprising a second optical sensor optically coupled to the active portion and extending away from the active portion between about 1 km and about 65 km.

18. The installation of claim 17, wherein the optical sensors define a region extending between about 100 km and about 130 km over which a disturbance can be detected by one or both of the sensors.

* * * * *

UNITED STATES PATENT AND TRADEMARK OFFICE
CERTIFICATE OF CORRECTION

| | |
|---|---|
| PATENT NO. | : 8,873,064 B2 |
| APPLICATION NO. | : 13/499274 |
| DATED | : October 28, 2014 |
| INVENTOR(S) | : Tapanes |

Page 1 of 1

It is certified that error appears in the above-identified patent and that said Letters Patent is hereby corrected as shown below:

In the Claims:

Col. 19, line 20 Claim 1 "...the second fiber portion via a third fiber coupler, (iii) a ..." should read – "...the second fiber portion, (iii) a ..."

Col. 19, line 26 Claim 1 "...third fiber portion, and (iv) a first polarization ..." should read – "...third fiber portion via a third fiber coupler, and (iv) a first polarization ..."

Signed and Sealed this
Thirtieth Day of June, 2015

Michelle K. Lee
*Director of the United States Patent and Trademark Office*